US00PP09994P

United States Patent [19]

Meilland

[11] Patent Number: Plant 9,994

[45] Date of Patent: Aug. 12, 1997

[54] CLIMBER ROSE PLANT NAMED 'MEIROUPIS'

[75] Inventor: Alain A. Meilland, Antibes, France

[73] Assignee: The Conard-Pyle Company, West Grove, Pa.

[21] Appl. No.: 706,497

[22] Filed: Sep. 4, 1996

[51] Int. Cl.[6] ..... A01H 5/00

[52] U.S. Cl. ..... Plt./5

[58] Field of Search ..... Plt./2, 5, 1, 22, Plt./26

*Primary Examiner*—Howard J. Locker

*Attorney, Agent, or Firm*—Burns, Doane, Swecker & Mathis, L.L.P.

[57] ABSTRACT

A new and distinct variety of climbing rose plant is provided which abundantly forms attractive fragrant ruffled pink blossoms. The plant exhibits a good capacity to rebloom. The blossoms are long-lasting and exhibit a good petal-drop propensity. The plant also exhibits dark green and glossy foliage, as well as good disease resistance. The new variety is particularly well suited for growing as attractive ornamentation in the landscape.

1 Drawing Sheet

SUMMARY OF THE INVENTION

The new variety of climbing rose plant was created by artificial pollination wherein two parents were crossed which previously had been studied in the hope that they would contribute the desired characteristics. The female parent (i.e., the seed parent) of the new variety was the product of the cross of the 'Meibeluxen' variety (non-patented in the United States) and the 'Friesia' variety (non-patented in the United States). The 'Friesia' variety sometimes is known as 'Sunsprite' and 'Korresia'. The male parent (i.e., the pollen parent) was the 'Prairie Princess' variety (non-patented in the United States). The parentage of the new variety can be summarized as follows:

('Meibeluxen'×'Friesia')×'Prairie Princess'.

The seeds resulting from the above pollination were sown and small plants were obtained which were physically and biologically different from each other. Selective study resulted in the identification of a single plant of the new variety.

It was found that the new variety of climbing rose plant of the present invention possesses the following combination of characteristics:

(a) forms in abundance attractive long-lasting fragrant ruffled pink blossoms,
(b) exhibits a good capacity to rebloom,
(c) forms attractive dark green and glossy foliage,
(d) exhibits good disease resistance, and
(e) is particularly well suited for growing as attractive ornamentation in the landscape.

The new variety well meets the needs of the horticultural industry and is particularly well adapted for use as an attractive climbing ornamental plant in an outdoors environment.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meiroupis' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa froebelii* understock and growing outdoors at Le Cannet des Maures, Var, France. Dimensions in centimeters are indicated at the bottom of the photograph.

FIG. 15 illustrates a specimen of two leaves with five leaflets — plan view — upper surface (left) and under surface (right); and FIG. 16 illustrates a specimen of a leaf with seven leaflets — plan view — under surface.

DETAILED DESCRIPTION

Figures 1, 2, 3, 4, 5, 6, 7, 8, 9, 10, 11, 12, 13, 14:
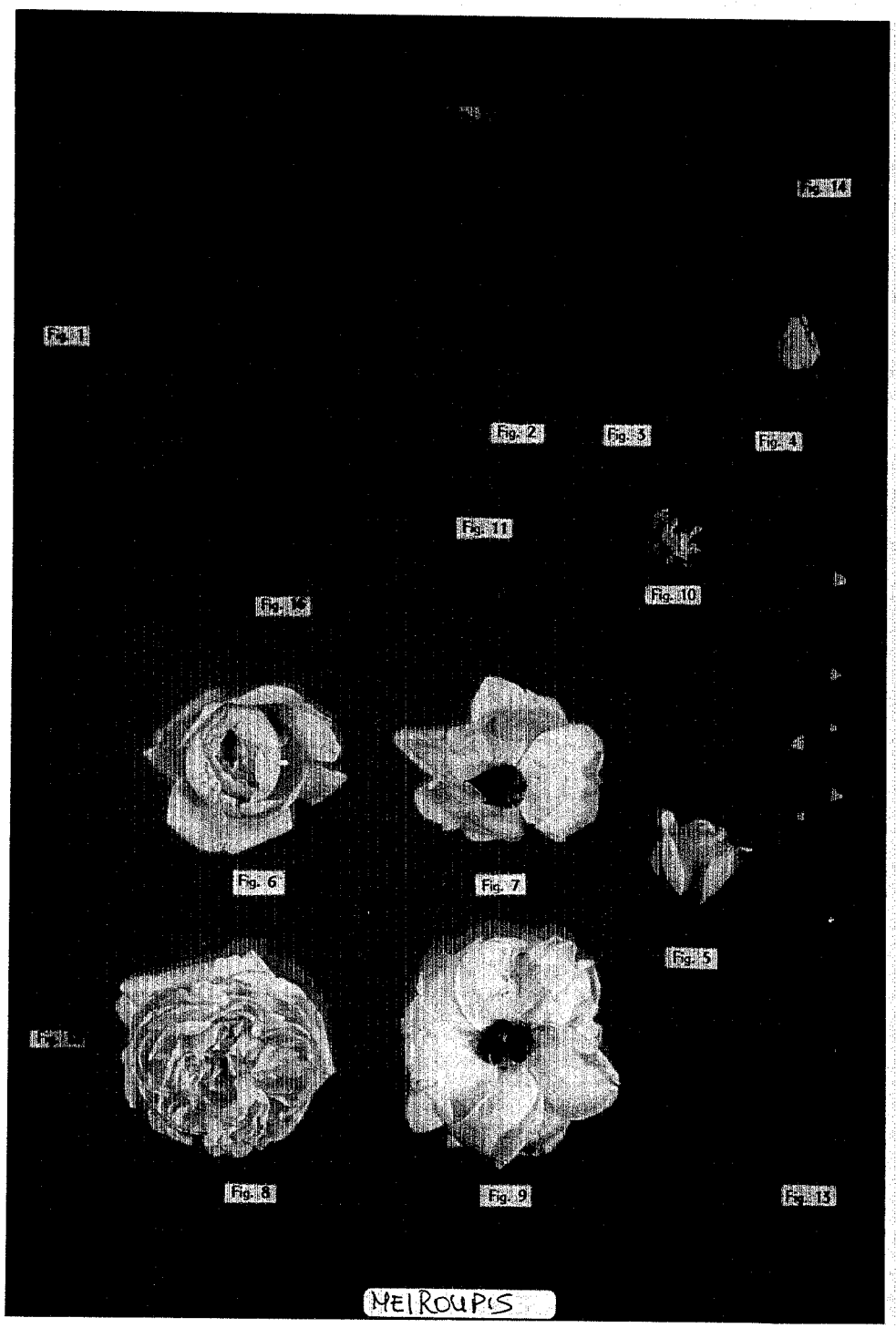
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.

The chart used in the identification of the colors is that of The Royal Horticultural Society (R.H.S. Colour Chart). The description is based on the observation of two year-old plants during September while budded on *Rosa froebelii* understock and growing outdoors at Le Cannet des Maures, Var, France. The coloration in common terms precedes reference to the chart in some instances.

Class: Climbing.

Plant:

*Height.*—Approximately 150 cm.

*Habit.*—Climbing.

Branches:

*Color.*—Young stems: near Green Group 143C. Adult wood: slightly darker than Green Group 143C.

*Thorns.*—Size: small to medium. Quantity: very numerous. Color: greenish on young stems and Havana brown on adult wood.

Leaves:

*Stipules.*—Adnate, pectinate, wide and linear.

*Petioles.*—Upper surface: striped reddish on young foliage, and medium green on adult foliage with more or less glandular edges. Under surface: rarely bear small thorns.

*Leaflets.*—Number: 3, 5, and 7 (most often). Shape: elliptic. Serration: single and regular (as illustrated). Texture: consistent. General appearance: dense, dark green, and glossy. Color (young foliage): Upper surface: near Green Group 137A. Under surface: near Green Group 137A. Color (adult foliage): Upper surface: near Green Group 137D. Under surface: near Green Group 137D.

Inflorescence:

*Number of flowers.*—Usually two to five per stem.

*Peduncle.*—Light green, more less stained with reddish coloration, aciculated, and the length is approximately 3.5 to 4.5 cm. on average.

*Sepals.*—Upper surface: tomentose, greenish, and widely tinted with reddish coloration. Under surface: light green in coloration and with a few extensions.

*Buds.*—Shape: conical. Length: approximately 2 cm. on average. Size: small. Color upon opening: Upper surface: near Azalea Pink, Red Group 38A, and commonly lightening at the edges. Under surface: near Azalea Pink, Red Group 38A, and commonly lightening at the edges.

*Flower.*—Shape: ruffled and similar to that of an old-fashioned rose. Diameter: approximately 7 to 8 cm. on average. Color (when opening begins): Upper surface: near Azalea Pink, Red Group 38A, and more or less suffused with Geranium Lake, Red Group 47D, with the edges commonly being near Empire Rose, Red Group 48D. Under surface: near Red Group 37A, and more or less suffused with Geranium Lake, Red Group 47D, with the edges commonly being Empire Rose, Red Group 48D. Color (when blooming): Upper surface: near Red Group 55D on the external petals and Coral Pink, Red Group 38D, suffused with Empire Rose, Red Group 48D, on the internal petals. Under surface: near Red Group 55D on the external petals and Coral Pink, Red Group 38D, suffused with Empire Rose, Red Group 48D, on the internal petals. Color (at end of opening): upper surface: near Red Group 55D on the external petals and Coral Pink, Red Group 38D, suffused with Empire Rose, Red Group 48D, on the internal petals. Under surface: near Red Group 55D on the external petals and Coral Pink, Red Group 38D, suffused with Empire Rose, Red Group 48D, on the internal petals. Fragrance: pleasant and of medium intensity. Lasting quality: long on the plant. Petal number: approximately 135 to 140 on average. Petal shape: rounded with a cordate base. Petal drop: good with the petals commonly detaching cleanly. Stamen number: commonly are absent. Pistils: approximately 75 on average. Stigmas: ochre in coloration. Styles: greenish in coloration. Receptacle: medium green, smooth, and in longitudinal section in the shape of a pitcher.

Development:

*Vegetation.*—Vigorous.

*Blooming.*—Abundant and reblooming.

*Resistance to diseases.*—Good.

I claim:

1. A new and distinct variety of climbing rose plant characterized by the following combination of characteristics:

(a) forms in abundance attractive long-lasting fragrant ruffled pink blossoms,
(b) exhibits a good capacity to rebloom,
(c) forms attractive dark green and glossy foliage,
(d) exhibits good disease resistance, and
(e) is particularly well suited for growing as attractive ornamentation in the landscape;

substantially as herein shown and described.

* * * * *

MEIROUPIS